United States Patent [19]

Seipp et al.

[11] 4,372,971
[45] Feb. 8, 1983

[54] HETEROCYCLIC PROSTAGLANDIN TYPE COMPOUNDS, MEDICAMENTS CONTAINING THEM AND PROCESSES FOR THE PREPARATION AND USE OF THESE HETEROCYCLIC COMPOUNDS AND MEDICAMENTS

[75] Inventors: Ulrich Seipp, Aachen; Werner Vollenberg, Stolberg; Bernd Mueller; Gudrun Michel, both of Aachen, all of Fed. Rep. of Germany

[73] Assignee: Gruenenthal GmbH, Stolberg, Fed. Rep. of Germany

[21] Appl. No.: 290,573

[22] Filed: Aug. 6, 1981

[30] Foreign Application Priority Data

Aug. 8, 1980 [DE] Fed. Rep. of Germany ....... 3029984

[51] Int. Cl.³ ................ A61K 31/557; C07D 307/935; A61K 31/34
[52] U.S. Cl. ..................................... 424/285; 542/429
[58] Field of Search ......................... 542/429; 424/285

[56] References Cited

U.S. PATENT DOCUMENTS

| | | | |
|---|---|---|---|
| 3,933,895 | 1/1976 | Nelson | 260/473 A |
| 3,933,896 | 1/1976 | Nelson | 260/473 A |
| 3,933,897 | 1/1976 | Nelson | 260/473 A |
| 3,933,898 | 1/1976 | Nelson | 260/473 A |
| 3,933,899 | 1/1976 | Nelson | 260/473 A |
| 3,933,900 | 1/1976 | Nelson | 260/473 A |
| 4,078,083 | 3/1978 | Babej et al. | 424/317 |
| 4,100,192 | 7/1978 | Morozowich | 260/558 |
| 4,150,222 | 4/1979 | Johnson | 542/426 |
| 4,207,257 | 6/1980 | Morozowich | 260/558 R |
| 4,238,623 | 12/1980 | Buckler | 560/53 |

FOREIGN PATENT DOCUMENTS

| | | |
|---|---|---|
| 800441 | 7/1980 | South Africa . |
| 2008581 | 6/1979 | United Kingdom . |
| 2025972 | 1/1980 | United Kingdom . |
| 2037752 | 7/1980 | United Kingdom . |

OTHER PUBLICATIONS

Shimoji et al., *Tetrahedron Letters*, vol. 21, pp. 1255–1258.
Nelson et al., *Prostaglandins*, vol. 10, No. 5, pp. 795–806, (Nov., 1975).
Honohan et al., *Prostaglandins*, vol. 19, No. 1, pp. 139–153, (Jan., 1980).

*Primary Examiner*—Henry R. Jiles
*Assistant Examiner*—Bernard Dentz
*Attorney, Agent, or Firm*—Schwartz, Jeffery, Schwaab, Mack, Blumenthal & Koch

[57] ABSTRACT

Disclosed are new heterocyclic compounds, medicaments containing them (for oral or parenteral administration) and processes for the preparation and use of these heterocyclic compounds and medicaments. The new compounds which particularly act as inhibitors of blood platelet aggregation and as blood pressure lowering agents correspond to the general formula

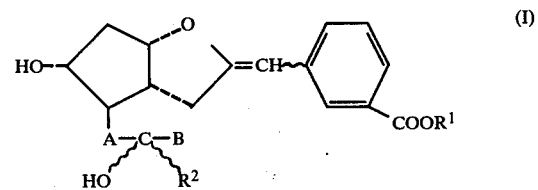

wherein $R^1$ is hydrogen, a cation or the residue of an alcohol, $R^2$ represents hydrogen or methyl, A is a member of the group consisting of the radicals —CH$_2$—CH$_2$—, (trans)—CH=CH— and —C≡C—, and wherein B represents an alkyl or a cycloalkyl radical. In these compounds the phenyl radical may be arranged with respect to the double bond in the E- and/or in the Z-configuration and at the carbon atom bearing the group $R^2$ (and others) may exist RS- or S-configuration. The compounds of formula I are prepared in a manner known per se starting from derivatives of 3α,5α-dihydroxycyclopentane-1α-acetaldehyde γ-lactol substituted accordingly and phosphonium salts of the formula

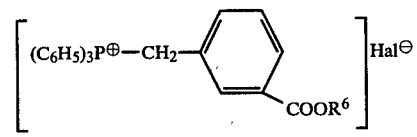

wherein $R^6$ represents hydrogen or alkyl and wherein Hal is chlorine, bromine or iodine.

42 Claims, No Drawings

HETEROCYCLIC PROSTAGLANDIN TYPE COMPOUNDS, MEDICAMENTS CONTAINING THEM AND PROCESSES FOR THE PREPARATION AND USE OF THESE HETEROCYCLIC COMPOUNDS AND MEDICAMENTS

BACKGROUND OF THE INVENTION

The present invention relates to new heterocyclic compounds, to pharmaceutical compositions containing these new compounds for oral or parenteral administration, to a process for preparing these new compounds and compositions and also to methods of pharmacological treatment utilizing the compounds and compositions according to the invention.

The compounds according to the present invention contain the same basic, chemical structure as prostacyclin, which occurs in nature. Prostacyclin possesses the properties of inhibiting blood platelet aggregation and lowering the blood pressure. These properties are exhibited at generally the same dosage level. Prostacyclin is not as stable as would be desirable.

SUMMARY OF THE INVENTION

It is therefore an object of the present invention to provide new chemical compounds which possess valuable pharmaceutical properties.

A further object of the invention resides in providing improved pharmaceutical compositions.

It is another object of the invention to provide a process for preparing the new compounds and compositions according to the invention.

Still another object of the invention is to provide an improved method of pharmacological treatment, in particular to inhibit blood platelet aggregation and to lower blood pressure.

In accomplishing the foregoing objects, there has been provided in accordance with the present invention a new class of heterocyclic compounds of the formula

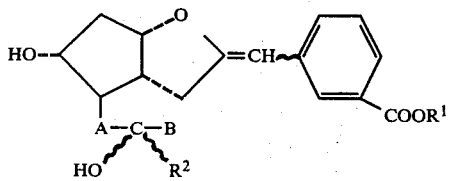

in which the phenyl radical with respect to the double bond has the E-, the EZ- or the Z-configuration and in which at the carbon atom 15 which carries the group $R^2$ there exists the RS- or S-configuration, wherein $R^1$ represents hydrogen, a pharmaceutically acceptable cation or the residue of an alcohol being pharmaceutically applicable in esterified form, $R^2$ represents hydrogen or a methyl group, A represents —$CH_2$—$CH_2$—, (trans)—CH=CH— or —C≡C—, and B represents an alkyl group containing 5 to 9 carbon atoms and having the structure

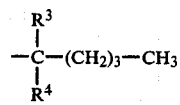

wherein $R^3$ and $R^4$ have the same or a different meaning and each represents hydrogen, methyl or ethyl, or B represents cyclohexyl or cyclohexyl substituted in position 4' by a methyl or an ethyl group.

In accordance with another aspect of the present invention, there has been provided a pharmaceutical composition, comprising a therapeutically effective amount of a heterocyclic compound as defined above as active ingredient and at least one pharmaceutically acceptable inert carrier or diluent.

In accordance with still another aspect of the present invention, there has been provided a process for preparing the heterocyclic compounds defined above, comprising the steps of reacting a compound of the formula

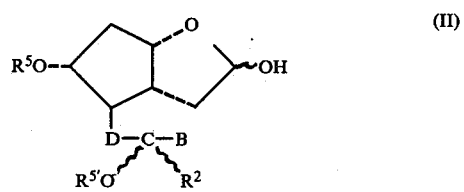

wherein B represents an alkyl group containing 5 to 9 carbon atoms and having the structure

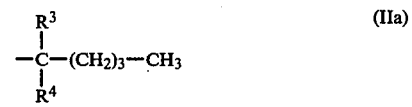

wherein $R^3$ and $R^4$ have the same or a different meaning and each represents hydrogen, methyl or ethyl, or B represents cyclohexyl or cyclohexyl substituted in position 4' by a methyl or an ethyl group, $R^2$ represents hydrogen or a methyl group, D represents —$CH_2$—$CH_2$—, (trans)—CH=CH— or —CH=CHal—, in which Hal represents chlorine, bromine or iodine and wherein $R^5$ and $R^{5'}$ have the same or a different meaning and each represents hydrogen or a protecting group cleavable under mild conditions, in the absence of oxygen at about 10° to 30° C. in the presence of a solvent containing a strong base, with a compound of the formula

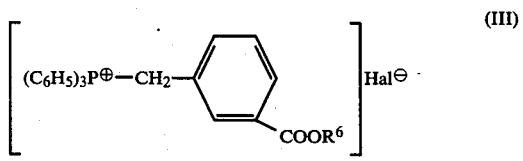

wherein $R^6$ is hydrogen or an alkyl group containing 1 to 6 carbon atoms, preferably methyl or ethyl, and wherein Hal represents chlorine, bromine or iodine; where $R^6$ is hydrogen, esterifying the group $COOR^6$ to the group $COOR^7$, wherein $R^7$ represents an alkyl group containing 1 to 6 carbon atoms; splitting off any protecting groups $R^5$ and $R^{5'}$ which are present under mild conditions to give a compound of the formula

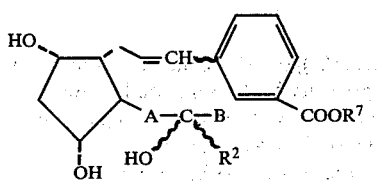
(IV)

halogenating and cyclizing the compound of formula IV by treatment at about 0°–30° C. with an electrophilic brominating or iodinating agent in the presence of an inert solvent and in the presence of an agent capable of binding acids to give a compound of the formula

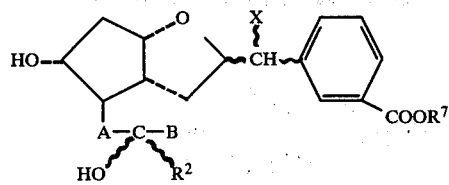
(V)

wherein A represents —$CH_2$—$CH_2$—, (trans)—CH=CH— or —C≡C—, and X represents bromine or iodine; and dehydrohalogenating the compound of formula V to give a compound of the formula

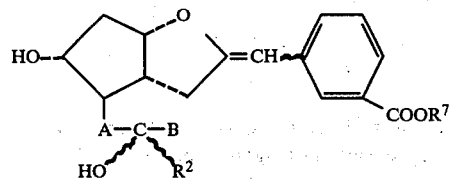
(Ia)

In accordance with still another aspect of the present invention there has been provided a method for inhibiting blood platelet aggregation, comprising the step of administering to a human patient a blood platelet aggregation inhibiting amount of a compound as defined above. Preferably, the method is for simultaneously inhibiting blood platelet aggregation and lowering blood pressure, comprising the step of administering to a human patient an amount of a compound as defined above, which is sufficient to simultaneously inhibit blood platelet aggregation and lower the blood pressure.

Further objects, features and advantages of the present invention will become apparent from the detailed description of preferred embodiments, which follows.

DETAILED DESCRIPTION OF PREFERRED EMBODIMENTS

The present invention relates to heterocyclic compounds of the formula

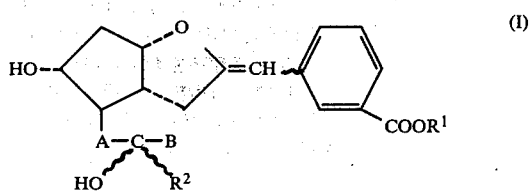
(I)

the basic structure of which, for example, is also contained in the naturally occurring prostacyclin.

In formula I, $R^1$ represents a hydrogen atom, a pharmaceutically acceptable cation or the residue of an alcohol being pharmaceutically applicable in esterified form, especially an alkyl radical having a straight or a branched chain of 1 to 6 carbon atoms. Preferably, $R^1$ represents, however, a methyl or an ethyl radical or, in case this group represents a cation, a sodium or a potassium cation. Other suitable cations are known from their use in the chemistry of prostaglandins or prostacyclin, respectively. For instance, there may be used the ions of calcium, magnesium, ammonium or of amines such as mono-, di- or trimethylamine, triethylamine, triethanolamine, trishydroxymethylamine and others. Furthermore, for the salt formation, basic amino acids like arginine or lysine may also be used.

$R^2$ represents hydrogen or a methyl radical. At the carbon atom (15) bearing the group $R^2$ (and others) there may exist RS- or S-configuration, with the 15S-forms of the compounds of formula I being preferred.

A is a member of the group consisting of the radicals —$CH_2$—$CH_2$—, (trans)—CH=CH— and —C≡C—. The two last mentioned radicals are preferred, and especially in the preferred 15S-forms of the compounds of formula I, A is preferably (trans)—CH=CH—.

B either represents an alkyl radical containing 5 to 9 carbon atoms and having the structure

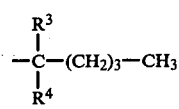

wherein $R^3$ and $R^4$ have the same or a different meaning and each represent hydrogen, methyl or ethyl or B represents a cyclohexyl radical which may be substituted in position 4' by a methyl or an ethyl radical. In preferred groups of compounds of formula I, B represents the cyclohexyl radical or the alkyl radical of the structure given above wherein both of $R^3$ and $R^4$ are hydrogen or methyl or wherein $R^3$ is ethyl and $R^4$ is hydrogen, respectively.

In the compounds of formula I the phenyl radical may be arranged with respect to the double bond in the E-, EZ- or preferably in the Z-configuration.

If A is as preferred the (trans)—CH=CH— radical, the compounds according to the invention correspond to the formula

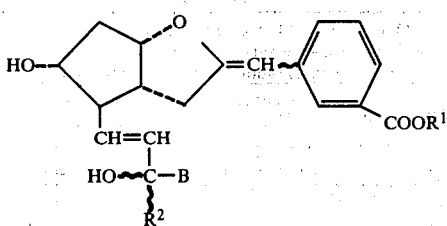

wherein $R^1$, $R^2$ and B have the same meaning as above. Accordingly, the especially preferred compounds of formula I in which A is the (trans)—CH=CH— radical and in which B is the alkyl or cycloalkyl radical mentioned above having the following structures

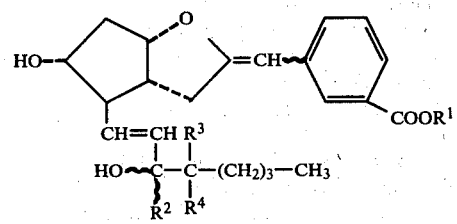

wherein $R^1$ to $R^4$ have the same meaning as above, and

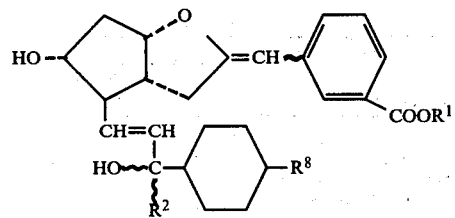

wherein $R^1$ and $R^2$ are as defined above and wherein $R^8$ represents hydrogen, methyl or ethyl.

With respect to the nomenclature of the compounds of formula I, reference is made to the papers of Nelson, *J. Med. Chem.* Vol. 17, 911 (1974), and Johnson et al., *Prostaglandins* Vol. 15, 737 (1978). Accordingly, the carbon atoms in the basic structure of the compounds of formula I are numbered as follows:

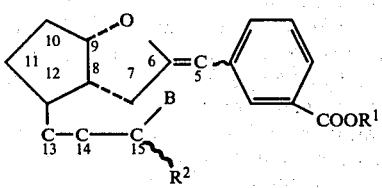

wherein in consideration of the definition given above for A the carbon atoms 13 and 14 may also be connected by a double or triple bond and wherein $R^1$, $R^2$ and B have the same meaning as in formula I. The numbering of the carbon atoms in $R^1$, $R^2$ and B needs no special explanation besides mentioning that in case B is a cyclohexyl radical, the carbon atoms thereof will become numbered as 1', 2', etc. (as may be seen also from the definition given for B hereinabove).

The compounds of formula I have prostacyclin-like properties with respect to blood platelet aggregation (in-vitro and in-vivo) and with respect to their effect on blood pressure; however, they distinguish from prostacyclin, for instance, in that they are far more stable than prostacyclin. Compared with 5,6-dihydroprostacyclin, which is considered a reference compound due to its chemical stability, e.g., the product obtained in Example 3b herein, is several times more active. Surprising for the compounds according to the invention is the relation of their blood platelet aggregation inhibiting effect to their blood pressure lowering activity. Contrary to 5,6-dihydroprostacyclin, which produces both these effects at the same dosage range, the compounds of formula I produce blood pressure lowering effects only after administering far higher dosages then those necessary to produce platelet aggregation inhibition, as may be seen from the following Tables 1a–1d in which, for some compounds of formula I, the experimentally-obtained (in the in-vivo-experiments each time using groups of 4 to 6 animals) values of the relative activity in comparison to 5,6-dihydroprostacyclin are given:

TABLE 1a

Relative activity against the aggregation of human thrombocytes induced by arachidonic acid in-vitro (the $IC_{50}$, i.e., the concentration causing under the experimental conditions in 50% of the cases inhibition of the platelet aggregation for 5,6-dihydroprostacyclin is 0.18 µMol/l):

| Test compound | 5,6-Dihydro-prostacyclin | PRODUCT OF EXAMPLE NO. | | | | | |
|---|---|---|---|---|---|---|---|
| | | 1e)ii) | 1e)i) | 2a | 2b | 3b | 4b |
| relative activity | 1.0 | 0.25 | 0.86 | 1.2 | 1.2 | 18.0 | 0.31 |

TABLE 1b

Relative activity on the ADP induced fall in platelet count in-vivo in narcotized rats (urethane narcosis; intravenous administration of the test compounds; the $ED_{50}$ for 5,6-dihydroprostacyclin under these experimental conditions is 0.0114 mg/kg):

| Test compound | 5,6-Dihydro-prostacyclin | PRODUCT OF EXAMPLE NO. | | | |
|---|---|---|---|---|---|
| | | 1e)ii) | 1e)i) | 3b | 4b |
| relative activity | 1.0 | 0.97 | 1.3 | 5.0 | 0.2 |

It is remarkable that especially the product of Example 3b is several times more active than 5,6-dihydroprostacyclin in-vitro (Table 1a) as well as in-vivo (Table 1b).

TABLE 1c

Relative blood pressure lowering activity in conscious, spontaneous hypertensive rats (measurement via in-dwelling catheter; intravenous administration of the test compounds; the $ED_{20}$ for 5,6-dihydroprostacyclin under these experimental conditions is 0.005 mg/kg):

| Test compound | 5,6-Dihydro-prostacyclin | PRODUCT OF EXAMPLE NO. | | | |
|---|---|---|---|---|---|
| | | 1e)ii) | 1e)i) | 3b | 4b |
| relative acti- | | | | | |

TABLE 1c-continued

Relative blood pressure lowering activity in conscious, spontaneous hypertensive rats (measurement via in-dwelling catheter; intravenous administration of the test compounds; the $ED_{20}$ for 5,6-dihydroprostacyclin under these experimental conditions is 0.005 mg/kg):

| Test compound | 5,6-Dihydro-prostacyclin | PRODUCT OF EXAMPLE NO. | | | |
|---|---|---|---|---|---|
| | | 1e)ii) | 1e)i) | 3b | 4b |
| vity | 1.0 | 0.014 | 0.1 | 0.25 | 0.012 |

TABLE 1d

Index of selectivity $\left(\dfrac{\text{aggregation inhibiting activity}}{\text{blood pressure lowering activity}}\right)$ in comparison to 5,6-dihydroprostacyclin (calculated from the values given in Tables 1b and 1c).

| Test compound | 5,6-Dihydro-prostacyclin | PRODUCT OF EXAMPLE NO. | | | |
|---|---|---|---|---|---|
| | | 1e)ii) | 1e)i) | 3b | 4b |
| Index of selectivity | 1.0 | 69.3 | 13.0 | 20.0 | 16.7 |

These results prove that the compounds of formula I can be used not only in diseases which an inhibition of platelet aggregation is desired without accompanying lowering of the blood pressure (as for instance hyperaggregability in coronary heart disease) but also in higher doses in diseases in which a simultaneous vasodilation is desired (as for instance ischaemic peripheral vascular disease).

Natural prostacyclin and also the chemically stable 5,6-dihydroprostacyclin produce only for a short time their aggregation inhibiting and blood pressure lowering activities. These compounds have therefor to be administered in therapeutic use by continuous infusion.

Surprisingly, the compounds of formula I produce considerably longer lasting effects than 5,6-dihydroprostacyclin, i.e., such that they are suitable also to produce long lasting platelet aggregation inhibition and blood pressure lowering on administration of (one or several consecutive) single doses as may be seen from the following Tables 2a and 2b:

TABLE 2a

Duration of the platelet aggregation inhibiting effect in-vivo (measured with the model of ADP induced fall in platelet count in narcotized rats on intravenous administration of the test compounds)

| Test compound | Dose (mg/kg) | Maximum effect % Aggregation inhibition | Effect in relation to maximum effect | |
|---|---|---|---|---|
| | | | 10 min. after administration | 30 min. after administration |
| 5,6-Dihydroprostacyclin | 0.1 | 62.4 = 100% | 33.8% | 0% |
| Example 1e)i) | 1.0 | 72.7 = 100% | 69.3% | 41.3% |
| Example 3b | 0.1 | 72.5 = 100% | 62.6% | 66.3% |
| Example 4b | 1.0 | 66.8 = 100% | 45.4% | 24.5% |

TABLE 2b

Duration of the blood pressure lowering effect in conscious, spontaneous hypertensive rats (intravenous administration of the test compounds):

| Test compounds | Dose (mg/kg) | Maximum effect % Blood pressure lowering | Effect in relation to maximum effect | |
|---|---|---|---|---|
| | | | 10 min. after administration | 30 min. after administration |
| 5,6-Dihydroprostacyclin | 0.0215 | 28 = 100% | 7.1% | 0% |
| Example 3b | 0.1 | 23 = 100% | 87.0% | 39.1% |
| Example 4b | 1.0 | 22 = 100% | 90.9% | 68.2% |

Prostaglandins like $PGE_2$ or $PGF_{2\alpha}$ cause contraction of the smooth muscle of the intestine and uterus and accordingly when administered in-vivo may induce diarrhea and abortion. Such effects are undesired side effects in compounds such as analogs of prostacyclin to be used in platelet aggregation inhibition and in blood pressure lowering.

The new compounds of formula I, in contrast to 5,6-dihydroprotacyclin, have only very weak contraction-inducing properties (as can be seen from the following Tables 3a and 3b). Accordingly, therapeutic use of doses sufficient to produce inhibition of platelet aggregation and lowering of the blood pressure causes no risk that such side effects may occur.

TABLE 3

Relative contraction inducing activities

| Test Compound | Relative contraction inducing activity |
|---|---|
| (a) tests on isolated rat uterus | |
| Prostaglandin $F_{2\alpha}$ | 100% ($EC_{50}$ 50.1 μM) |
| 5,6-Dihydroprostacyclin | 26.1% |
| Product of Example 1e)i) | 0.58% |
| (b) tests on isolated rat colon | |
| Prostaglandin $F_{2\alpha}$ | 100% ($EC_{50}$ 50.14 μM) |
| 5,6-Dihydroprostacyclin | 23.8% |
| Product of Example 1e)i) | 0.002% |

Similar results were obtained also in testing other compounds of formula I.

Inasmuch the compounds of formula I not only possess surprising and valuable biological properties but also a good chemical stability, they may be used for parenteral and also for oral application to humans and mammals to produce an inhibition of blood platelet aggregation in therapy and prophylaxis of diseases in which blood platelet aggregation and/or a hyper-aggregability are of pathogenetic importance. Such diseases are, for instance, arterial thromboses in vascular endothelial disorders, atherosclerosis, hemostatic arterial and venous thromboses and myocardial infarction. Due to their influence on the blood pressure, the compounds of formula I are suitable also for the treatment of pulmonary as well as of systemic hypertension. The comdpounds according to the invention are useful for diminuation of platelet aggregability in artificial extracorporeal circulations and perfusion of isolated body portions (e.g., in dialysis, cardiopulmonary bypass, transplantations etc.) wherein the compounds are added in micromolar concentrations to the patients blood.

The invention accordingly relates also to medicaments (i.e., pharmaceutical compositions) containing as active ingredients one or more of the heterocyclic compounds of formula I. The compound content of the individual dose is between about 0.01 and 10 mg, whereby preferably compositions for parenteral administration contain about 0.01–1 mg and those for oral administration contain about 0.1–10 mg. The medicaments to be used for parenteral administration may be solutions or suspensions but may also be dry formulations suitable for easy reconstitution, as for instance, lyophylized sodium salts of compounds of formula I in single dosage form.

For oral administration, tablets, pills, dragees, capsules, and similar application forms including, for example, those from which the active ingredients have a delayed release are suitable. In production of these pharmaceutical compositions, generally used inorganic or organic adjuvants such as diluents, carriers, binders, lubricants and others are added to the compounds of the general formula I.

The pharmaceutical compositions of the invention are prepared in accordance with accepted standards in a manner known per se. It should be mentioned that the compositions for parenteral use have to be sterile and, if prepared in liquid form, isotonic condition.

A further aspect of the invention involves the preparation of the compounds of formula I. The starting material is a lactol of the formula

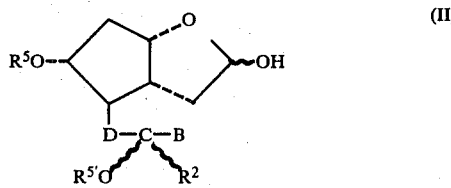

which may be in the 15S-form and wherein B and $R^2$ have the same meaning as in formula I, D is a member of the group consisting of the radicals —$CH_2$—$CH_2$—,(trans)—CH=CH— and —CH=CHal—, in which Hal represents chlorine, bromine or iodine, and wherein $R^5$ and $R^{5'}$ have the same or a different meaning and represent hydrogen or a protecting group which can easily split off, as for instance, a tetrahydropyranyl group (THP) or a trimethyl silyl group (TMS).

The lactol formula II is reacted at about 10° to 30° C., in the presence of a solvent containing a strong base and in the absence of oxygen, with a phosphonium salt of the formula

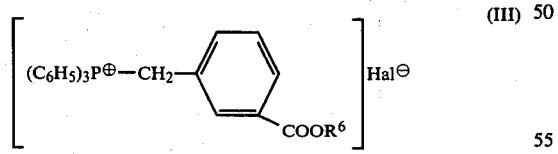

wherein $R^6$ is hydrogen or an alkyl residue with 1 to 6 carbon atoms, preferably methyl or ethyl, and wherein Hal represents chlorine, bromine or iodine, preferably bromine, followed—if $R^6$ is a hydrogen atom—by esterification of the carboxylic group $COOR^6$, preferably by treatment with diazomethane at about 0°–30° C., and finally splitting off the groups $R^5$ and $R^{5'}$ (if different from hydrogen) using mild conditions.

Strong bases which may be added during the condensation reaction are preferably butyl lithium, sodium hydride or potassium tert.-butoxide which are used in the presence of solvents, as for instance, dimethylsulfoxide, ether, tetrahydrofurane, dimethylformamide and the like.

The compound of formula III is used in an amount of 1 to 6 moles per mole of the compound of formula II, using 2 or more moles in case D represents the radical —CH=CHal—, because in this case under the conditions of the reaction this radical is transformed (with elimination of the respective hydrogen halide) to the group —C≡C—.

The presence of oxygen is preferably prevented by working in an atmosphere of inert gases, like argon or nitrogen.

The reaction is performed in about 1 to 12 hours and may be controlled as usual by chromatography.

To the reaction mixture there is preferably added a small, catalytically acting amount of a carboxylic acid, such as formic acid, acetic acid, propionic acid, bromoacetic acid, trichloroacetic acid or trifluoroacetic acid or, for instance, phenyl acetic acid, p-nitrobenzoic acid, p-chlorobenzoic acid or p-methoxybenzoic acid and especially the unsubstituted benzoic acid.

If $R^5$ or $R^{5'}$, respectively, represent protecting groups, these may be split off by treating for 1 to 5 hours at 30° to 50° C. with a mixture of tetrahydrofurane, glacial acetic acid and water in the relation 1:3:1.

Thus, a compound is obtained having the formula

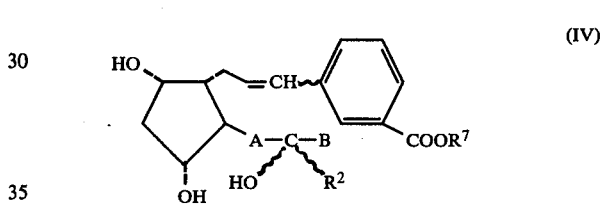

wherein $R^2$, A and B have the same meaning as in formula I and wherein $R^7$ is an alkyl radical having 1 to 6 carbon atoms.

If desired, this compound may be separated into the 15R- and 15S-isomers by column chromatography with silica gel.

The obtained products of formula IV are then halogenated and cyclisized in a conventional manner by treatment at about 0°–30° C. with an electrophilic reagent, such as for instance, iodine, iodine-potassium iodide or N-bromosuccinimide, in the presence of an inert solvent and possibly in the presence of water with addition of an agent capable of binding acids, to give a compound of formula V:

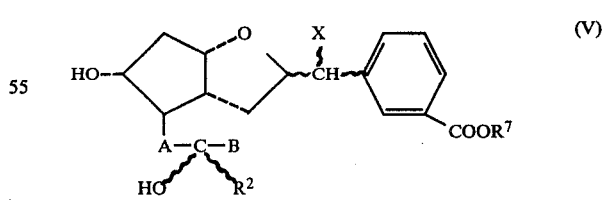

wherein $R^2$, $R^7$, A and B have the same meaning as above and wherein X represents a bromine or an iodine atom. Preferably X is an iodine atom and $R^7$ is a methyl or an ethyl radical.

Solvents which may be used in this reaction are, for instance, diethylether, tetrahydrofurane, dichloromethane, chloroform or mixtures of these solvents. The reaction is performed within about 30 minutes to 12 hours, and its progress may be supervised as usual by chromatography.

Agents capable of binding acids which may be used in this reaction are, for instance, sodium hydrogen carbonate, sodium carbonate, potassium carbonate, magnesium oxide or calcium carbonate.

On treating the compound of formula V with 1 to 5 moles of a base at temperatures of 0° to 90° C. for about 4 to 12 hours, dehydrohalogenation occurs, and a compound is formed having the formula:

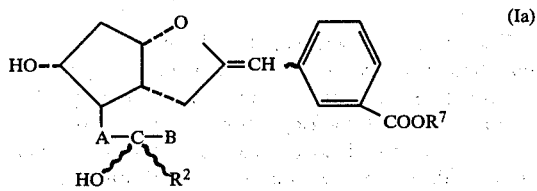

wherein $R^2$, $R^7$, A and B have the same meaning as above and which may be saponified at the group $COOR^7$ to give a compound of formula I in which $R^1$ is hydrogen or a cation.

Preferably, the reaction of the compound of formula V with the base is conducted at 0°-30° C. To induce the dehydrohalogenation, the following bases are especially suitable: sodium hydroxide, potassium hydroxide, sodium methoxide, sodium ethoxide, potassium tert.-butoxide as well as triethylamine, dicyclohexylamine, 1,5-diazabicyclo-(4,3,0)-non-5-ene (DBN) or 1,5-diazabicyclo-(5,4,0)-undec-5-ene (DBU) and others. This reaction may be conducted in the absence or in the presence of a solvent, such as toluene, methanol or ethanol.

The saponification of the ester group $COOR^7$ is preferably performed in aqueous-alcoholic solutions (like mixtures of water and methanol or ethanol) at 10° to 50° C. in the presence of 1 to 5 moles of sodium- or potassium hydroxide, calculated on the amount of compound of formula Ia present in the reaction mixture. The reaction is completed in about 6 to 48 hours. It is also possible to perform the dehydrohalogenation and the saponification of the ester group in the same reaction vessel without intermediate isolation of the compound of formula Ia.

The compounds of formula I in which $R^1$ is a cation obtained by saponification of compounds of formula Ia may [if desired after separating the 5E- and 5Z-isomers by means of high performance liquid chromatography (HPLC) using "reversed-phase"-conditions] be transformed in a manner known per se into other salts, for instance, by ion exchange chromatography.

The starting materials of formulae II and III, respectively, are obtained as described in the literature or in an analogous manner as follows:

(A) Phosphonium salts of formula III

Stoichiometric amounts of the respective aralkyl halogenides and of triphenylphosphine are dissolved in acetonitrile and boiled for 90 minutes. After evaporation at 50°-70° C. in a vacuum, the solid residue is thoroughly washed with cold acetone and, if necessary, recrystallized from water. Thus, e.g., the m-carboxyphenylmethyl triphenyl phosphoniumbromide, melting at 256°-258° C., was obtained.

(B) 3α,5α-Dihydroxy-2β[(3RS)-3-hydroxy-3-methyl-trans-1-octenyl]-cyclopentane-1α-acetaldehyde γ-lactol 3-trimethylsilyl ether was obtained as described by E. W. Yankee et al. in *J.A.C.S.*, Vol. 96, 5865–5876 (1974).

(C) The preparation of the starting materials of formula II is described in the following publications or may be made in an analogous manner, respectively:

| | |
|---|---|
| 15-Alkyl | E. W. Yankee et al. J.A.C.S., Vol. 96, 5865 (1974) |
| 15-H | E. J. Corey et al. J.A.C.S., Vol. 91, 5675 (1969) |
| 13,14-Dihydro | German Offenlegungsschrift No. 23 55 540 |
| 13,14-Dehydro | Belgian Patent No. 832 891 |
| 16-Alkyl and 16,16-Dialkyl 15(4'-Alkylcyclohexyl) | German Offenlegungsschrift No. 22 17 044 Belgian Patent No. 782 822 |

The following non-limiting examples serve further to illustrate the invention. No importance was attached to obtaining maximum yields in carrying out the experiments on which the examples are based. All temperature references are uncorrected. The nuclear magnetic spectra were measured (proton spectra at 60 MHz) with commercially available equipment. The $R_f$-values were determined by thin layer chromatography on silica gel.

EXAMPLE 1

(a) [(5EZ, 13E, 9α, 11α, 15RS)-2,3,4-trinor-1,5-inter-m-phenylene-9,11,15-trihydroxy-15-methyl]-prosta-5,13-dienoic acid.

1.8 ml of butyllithium (15% solution in hexane) are added dropwise with exclusion of humidity and in an atmosphere of nitrogen to 25 ml of dry dimethylsulfoxide, and the mixture is stirred for 30 minutes. Thereafter, while stirring, a solution of 670 mg of m-carboxyphenylmethyl triphenyl phosphoniumbromide and of 67 mg of benzoic acid in 10 ml of dry dimethylsulfoxide is added dropwise.

15 minutes later a solution of 500 mg of 3α,5α-dihydroxy-2β-[(3RS)-3-hydroxy-3-methyl-trans-1-octenyl]-cyclopentane-1α-acetaldehyde γ-lactol-3-trimethylsilyl ether in 5 ml of dimethylsulfoxide is added dropwise. The reaction mixture is stirred at room temperature for 12 hours and then poured into a saturated solution of sodium chloride in water. The mixture is extracted three times with ethyl acetate, the extracts being discarded. The aqueous solution is acidified to pH 4 by adding dilute hydrochloric acid and is then extracted thoroughly several times with ethyl acetate. The thus-obtained organic layers are combined, washed with water, dried over magnesium sulfate and finally evaporated at 40° C. in a vacuum, preferably using a rotation evaporator.

The raw product (520 mg) is purified by colum chromatography on silica gel using a mixture of ethyl acetate with glacial acetic acid in the proportion 99.5:0.5 as eluent. Thus 300 mg of the desired product are obtained in the form of a slightly yellowish oil.

$R_f$=0.125 (toluene-dioxane-glacial acetic acid 68:32:0.5)

Chemical shifts are given in ppm.
$^1$H-NMR (CDCl$_3$): (0.87,t,3H); (1.27,s,3H); (3.63-4.36,m.5H) (5.36-5.6,m,2H); (5.6-6.5,m,2H); (7.2-7.5,m,2H); (7.5-8.03,m,2H).

$^{13}$C-NMR (methanol-d$_4$): 27.271 (15S-Me); 28.184 (15R-Me)

(b) [(5EZ, 13E, 9α, 11α, 15RS)-2,3,4-trinor-1,5-inter-m-phenylene-9,11,15-trihydroxy-15-methyl]-prosta-5,13-dienoic acid methyl ester.

| (General formula IV: | $R^2 = CH_3$; $R^7 = CH_3$; A = (trans)-CH=CH—; B = n-$C_5H_{11}$) |
|---|---|

370 mg of the compound prepared according to Example 1a are dissolved in 50 ml of diethylether. While stirring, this solution is treated with a solution of diazomethane in ether until the evolution of nitrogen ceases. Thereafter, the yellowish reaction mixture is treated with an aqueous solution of sodium hydrogen carbonate while stirring. The colorless ethereal extract is separated, dried over magnesium sulfate and evaporated under vacuum at 30° C. The remaining slightly yellowish oil (350 mg) in thin layer chromatography gives two main spots having $R_f$ 0.48 and 0.55, respectively, (diethyletheracetonitrile 3:2). By column chromatography of the crude product on silica gel with diethylether-acetonitrile 3:2 two isomeric compounds are obtained being the desired 15S-isomer of the title compound and the 15R-isomer which becomes discarded.

The 15S-isomer is obtained in a yield of 130 mg. Its $R_f$-value is 0.48 (diethylether-acetonitrile 3:2).

$^1$H-NMR (CDCl$_3$): (0.87,t,3H); (1.27,s,3H); (3.7–4.43,m,3.9,s,5H); (5.37–5.6,m,2H); (5.6–6.73,m,2H); (7.2–7.5,m,2H); (7.67–8,m,2H).

$^{13}$C-NMR (methanol-d$_4$): 27.454

(c) [(13E, 5RS, 6RS, 9α, 11α, 15S)-2,3,4-Trinor-1,5-inter-m-phenylene-5-iodo-6,9-epoxy-11,15-dihydroxy-15-methyl]-prost-13-enoic acid methyl ester.

| (General formula V: | $R^2 = R^7 = CH_3$; X = I; A = (trans)-CH=CH—; B = n-$C_5H_{11}$) |
|---|---|

To a solution of 720 mg of iodine in a mixture of 6 ml of diethyl ether and 2 ml of saturated sodium hydrogencarbonate solution is added at room temperature in the dark while stirring a solution of 170 mg of the product of Example 1b in 2 ml of diethylether. The reaction mixture is stirred in the dark for 45 minutes and then treated with sodium thiosulfate solution until colorless. After pouring into an ice-cold aqueous saturated solution of sodium chloride the reaction mixture is three times extracted with 20 ml of diethyl ether each time.

The combined ether layers are dried over magnesium sulfate and finally evaporated in a rotation evaporator in a vacuum in the dark without heating. The crude product, obtained in the form of 180 mg of a yellowish oil having $R_f$=0.58 (ethyl acetate) is used in the next step without purification.

(d) [(5EZ, 13E, 9α, 11α, 15S)-2,3,4-trinor-1,5-inter-m-phenylene-6,9-epoxy-11,15-dihydroxy-15-methyl]-prosta-5,13-dienoic acid methylester.

| (General formula I: | $R^1 = R^2 = CH_3$; A = (trans)-CH=CH; B = n-$C_5H_{11}$) |
|---|---|

180 mg of the compound obtained in Example 1C are dissolved in 2 ml of toluene and, after addition of 100 μl of DBN, stirred in the dark for 4½ hours.

Thereafter, the toluene is eliminated by a stream of nitrogen at room temperature. The residue by column chromatography on silica gel with ethyl acetate gives 90 mg of a slightly yellowish oil which consists of two components having $R_f$-values of 0.55 and 0.6, respectively (ethyl acetate).

(e) Sodium salt of [(5EZ, 13E, 9α, 11α, 15S)-2,3,4-trinor-1,5-inter-m-phenylene-6,9-epoxy-11,15dihydroxy-15-methyl)]-prosta-5,13-dienoic acid.

| (General formula I: | $R^1$ = Na; $R^2 = CH_3$; A = (trans)-CH=CH—; B = n-$C_5H_{11}$) |
|---|---|

90 g of the product obtained in Example 1d are dissolved in 1 ml of methanol. After addition of 600 μl of 1 N-NaOH the mixture is stirred for 12 hours at 30°–40° C.

$R_f$ 0.36 and 0.44 (methanol-water 80:20)

By high performance liquid chromatography using methanol-water 40:60 on silica gel RP-18 (a brand of E. Merck AG, Darmstadt, Germany) and lyophilization of the eluate there are obtained:

(i) Sodium salt of [(5Z, 13E, 9α, 11α, 15S)-2,3,4-trinor-1,5-inter-m-phenylene-6,9-epoxy-11,15-dihydroxy-15-methyl]-prosta-5,13-dienoic acid.

yield 35 mg $R_f$=0.36 (methanol-water 80:20)

$^1$H-NMR (methanol-d$_4$): (0.9,t,3H); (1.28,s,3H); (3.63–4.2,m,1H); (5.28,s,broadened,1H); (5.5–5.73,m,2H); (7.06–7.48,m,1H); (7.53–7.8,m,2H); (7.96–8.1,m,1H).

(ii) Sodium salt of [(5E, 13E, 9α, 11α, 15S)-2,3,4-trinor-1,5-inter-m-phenylene-6,9-epoxy-11,15-dihydroxy-15-methyl]-prosta-5,13-dienoic acid:

yield 18 mg $R_f$=0.44 (methanol-water 80:20)

$^1$H-NMR (methanol-d$_4$): (0.9,t,3H); (1,3,s,3H); (3.56–4.16,m,1H); (5.5–5.7,m,2H); (5.9,s,broadened,1H); (7.13–7.48,m,2H); (7.53–7.9,m,2H).

EXAMPLE 2

By using the procedure described in Example 1 and the appropriate starting materials there are obtained (a) Sodium salt of [(5E, 13E, 9α, 11α, 15S)-2,3,4-trinor-1,5-inter-m-phenylene-6,9-epoxy-11,15-dihydroxy]-prosta-5,13-dienoic acid

| (General formula I: | $R^1$ = Na; $R^2$ = hydrogen; A = (trans)-CH=CH—; B = n-$C_5H_{11}$) |
|---|---|

$^1$H-NMR (methanol-d$_4$): (0.9,t,3H); (1.3,s,3H); (3.6–4.15,m,2H); (5.5–5.7,m,2H); (5.85–6.05,s,-broadened,1H); (7.15–7.5,m,2H); (7.5–8,m,2H).

$R_f$=0.44 (methanol-water 80:20)

(b) Sodium salt of [(5Z, 13E, 9α, 11α,15S)-2,3,4-trinor-1,5-inter-m-phenylene-6,9-epoxy-11,15-dihydroxy]-prosta-5,13-dienoic acid

| (General formula I: | $R^1$ = Na; $R^2$ = hydrogen; A = (trans)-CH=CH—; B = n-$C_5H_{11}$) |
|---|---|

¹H-NMR (methanol-d₄): (0.9,t,3H); (3.5–4.1,m,3H); (5.25,s,broadened,1H); (5.45–5.7,m,2H); (7–7.5,m,1H) (7.5–7.85,m,2H); (8,s,broadened,1H)

$R_f$=0.34 (methanol-water 80:20)

EXAMPLE 3

On following the procedure described in Example 1, there are obtained from m-carboxyphenyl-methyl-triphenylphosphonium bromide and the respective compound of formula II:

(a) Sodium salt of [(5E, 13E, 9α, 11α, 15S)-2,3,4-trinor-1,5-inter-m-phenylene-6,9-epoxy-11,15-dihydroxy-15-cyclohexyl-16,17,18,19,20-pentanor]-prosta-5,13-dienoic acid.

| (General formula I: | $R^1$ = Na; |
| | $R^2$ = hydrogen; |
| | A = (trans)-CH=CH—; |
| | B = cyclohexyl) |

¹H-NMR (methanol-d₄): (3.65–4.1,m,3H); (5.5–5.7,m,2H); (5.97,s,broadened,1H); (7.2–7.5,m,2H); (7.5–8,m,2H)

$R_f$=0.52 (methanol-water 80:20)

(b) Sodium salt of [(5Z, 13E, 9α, 11α, 15S)-2,3,4-trinor-1,5-inter-m-phenylene-6,9-epoxy-11,15-dihydroxy-15-cyclohexyl-16,17,18,19,20-pentanor]-prosta-5,13-dienoic acid.

| (General formula I: | $R^1$ = Na; |
| | $R^2$ = hydrogen; |
| | A = (trans)-CH=CH—; |
| | B = cyclohexyl) |

¹H-NMR (methanol-d₄): (3.67–3.95,m,2H); (4–4.2,m,2H); (5.37,s,broadened,1H); (5.5–5.7,m,2H); (7.15–7.4,m,1H); (7.6–8.15,m,3H).

$R_f$=0.38 (methanol-water 80:20)

EXAMPLE 4

By using the appropriate reactents and otherwise proceeding as described in the preceding examples, there are obtained:

(a) Sodium salt of [(5E, 13E, 9α, 11α, 15S, 16RS)-2,3,4-trinor-1,5-inter-m-phenylene-6,9-epoxy-11,15-dihydroxy-16-ethyl]-prosta-5,13-dienoic acid.

| (General formula I: | $R^1$ = Na; |
| | $R^2$ = hydrogen; |
| | A = (trans)-CH=CH—; |
| | B = —C($R^3$,$R^4$)—(CH₂)₃—CH₃, wherein |
| | $R^3$ is C₂H₅ and $R^4$ is hydrogen) |

¹H-NMR (methanol-d₄): (0.9,t,6H); (3.6–4.2,m,3H); (5.5–5.7,m,2H); (5.95,s,broadened,1H); (7.15–7.35,m.2H); (7.6–7.95,m,2H).

$R_f$=0.68 (methanol-water 80:20).

(b) Sodium salt of [(5Z, 13E, 9α, 11α, 15S, 16RS)-2,3,4-trinor-1,5-inter-m-phenylene-6,9-epoxy-11,15-dihydroxy-16-ethyl]-prosta-5,13-dienoic acid.

| (General formula I: | $R^1$ = Na; |
| | $R^2$ = hydrogen; |
| | A = (trans)-CH=CH—; |
| | B = —CH(C₂H₅)—(CH₂)₃—CH₃) |

¹H-NMR (methanol-d₄): (0.9,t,6H); 3.75–4.55,m,3H); (5.35,s,broadened,1H); (5.5–5.7,m,2H); (7.1–7.4,m,1H) (7.55–7.95,m,1H); (8.05,m,1H)

$R_f$=0.63 (methanol-water 80:20).

EXAMPLE 5

The procedure is the same as described in Example 1, whereby, however, m-carboxyphenylmethyl triphenyl phosphoniumbromide and 3α,5α-dihydroxy-2β-[(3RS)-3-hydroxy-1-octyl]-cyclopentane-1α-acetaldehyde γ-lactol bis-tetrahydropyranylether are used as reactants of general formula III and II, respectively. Thus, there are obtained:

(a) Sodium salt of [(5E, 9α, 11α, 15RS)-2,3,4-trinor-1,5-inter-m-phenylene-6,9-epoxy-11,15-dihydroxy]-prosta-5-enoic acid.

| (General formula I: | $R^1$ = Na; |
| | $R^2$ = hydrogen; |
| | A = —CH₂—CH₂—; |
| | B = n-C₅H₁₁) |

¹H-NMR (methanol-d₄): (0.9,t,3H); (5.9,s,broadened,1H); (7.18–8.15,m,4H); No signal at 5.5–5.7.

$R_f$=0.48 (methanol-water 80:20).

(b) Sodium salt of [(5Z, 9α, 11α, 15RS)-2,3,4-trinor-1,5-inter-m-phenylene-6,9-epoxy-11,15-dihydroxy]-prosta-5-enoic acid.

| (General formula I: | $R^1$ = Na; |
| | $R^2$ = hydrogen; |
| | A = —CH₂—CH₂—; |
| | B = n-C₅H₁₁) |

¹H-NMR (methanol-d₄): (0.9,t,3H); (5.3,s,broadened,1H); (7.1–8.05,m,4H); No signal at 5.5–5.7.

$R_f$=0.41 (methanol-water 80:20).

Following the procedures described above, especially those explained in the examples, the following compounds of formula I are prepared:

Potassium salt of [(5EZ, 13E, 9α, 11α, 15S)-2,3,4-trinor-1,5-inter-m-phenylene-6,9-epoxy-11,15-dihydroxy]-prosta-5,13-dienoic acid;

Sodium salt of [(5EZ, 13E, 9α, 11α, 15S)-2,3,4-trinor-1,5-inter-m-phenylene-6,9-epoxy-11,15-dihydroxy-16,16-dimethyl]-prosta-5,13-dienoic acid;

Potassium salt of [(5EZ, 13E, 9α, 11α, 15S, 16RS)-2,3,4-trinor-1,5-m-phenylene-6,9-epoxy-11,15-dihyrdoxy-16-ethyl]-prosta-5,13-dienoic acid;

Potassium salt of [(5EZ, 13E, 9α, 11α, 15S)-2,3,4-trinor-1,5-inter-m-phenylene-6,9-epoxy-11,15-dihydroxy-15-cyclohexyl-16,17,18,19,20-pentanor]-prosta-5,13-dienoic acid;

Sodium salt of [5EZ, 13E, 9α, 11α, 15S, 4'-trans)-2,3,4-trinor-1,5-inter-m-phenylene-6,9-epoxy-11,15-dihydroxy-15-(4'-methyl-cyclohexyl)-16,17,18,19,20-pentanor]-prosta-5,13-dienoic acid;

Potassium salt of [(5EZ, 13E, 9α, 11α, 15S, 4'-trans)-2,3,4-trinor-1,5-inter-m-phenylene-6,9-epoxy-11,15-dihydroxy-15-(4'-ethyl-cyclohexyl)-16,17,18,19,20-pentanor]-prosta-5,13-dienoic acid;

Sodium salt of [(5EZ, 9α, 11α, 15S)-2,3,4-trinor-1,5-inter-m-phenylene-6,9-epoxy-11,15-dihydroxy]-prosta-5-en-13-ynoic acid;

Sodium salt of [(5EZ, 9α, 11α, 15S)-2,3,4-trinor-1,5-inter-m-phenylene-6,9-epoxy-11,15-dihydroxy-15-cyclohexyl-16,17,18,19,20-pentanor]-prosta-5-enoic acid;

Sodium salt of [(5EZ, 9α, 11α, 15S)-2,3,4-trinor-1,5-inter-m-phenylene-6,9-epoxy-11,15-dihydroxy-15-cyclohexyl-16,17,18,19,20-pentanor]-prosta-5-en-13-ynoic acid;

Sodium salt of [(5EZ, 13E, 9α, 11α, 15S)-2,3,4-trinor-1,5-inter-m-phenylene-6,9-epoxy-11,15-dihydroxy-15-methyl-15-cyclohexyl-16,17,18,19,20-pentanor]-prosta-5,13-dienoic acid.

What is claimed is:

1. A heterocyclic compound of the formula

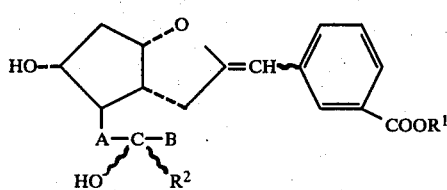
(I)

in which the phenyl radical with respect to the double bond has the E-, the EZ- or the Z-configuration and in which at the carbon atom 15 which carries the group $R^2$ there exists the RS- or S-configuration, wherein $R^1$ represents hydrogen, an alkyl group containing 1 to 6 carbon atoms or a pharmaceutically acceptable cation, $R^2$ represents hydrogen or a methyl group, A represents —$CH_2$—$CH_2$—, (trans)—CH=CH— or —C≡C—, and B represents an alkyl group containing 5 to 9 carbon atoms and having the structure

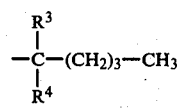

wherein $R^3$ and $R^4$ have the same or a different meaning and each represents hydrogen, methyl or ethyl, or B represents cyclohexyl or cyclohexyl substituted in position 4' by a methyl or an ethyl group.

2. A compound according to claim 1, having the formula

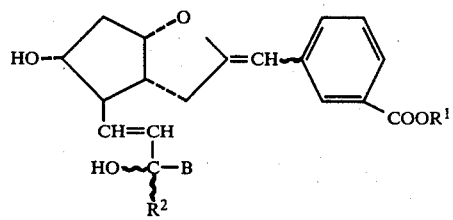

wherein $R^1$, $R^2$ and B have the same meaning as in claim 1.

3. A compound according to claim 1, having the formula

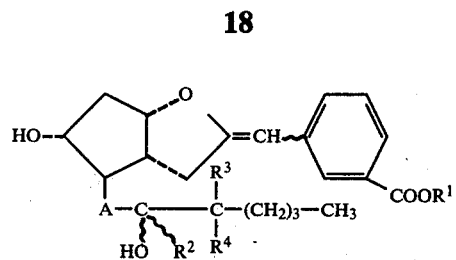

wherein $R^1$ to $R^4$ and A have the same meaning as in claim 1.

4. A compound according to claim 1, having the formula

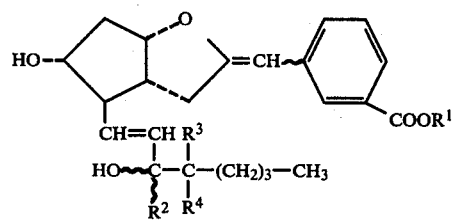

wherein $R^1$ to $R^4$ have the same meaning as in claim 1.

5. A compound according to claim 3 or 4, wherein $R^3$ and $R^4$ represent hydrogen.

6. A compound according to claim 3 or 4, wherein $R^3$ is a hydrogen atom and $R^4$ represents an ethyl radical.

7. A compound according to claim 1, having the formula

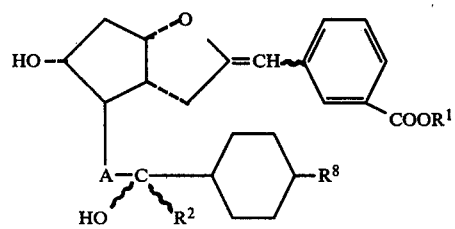

wherein $R^1$, $R^2$ and A have the same meaning as in claim 1 and wherein $R^8$ represents hydrogen, methyl or ethyl.

8. A compound according to claim 1, wherein $R^2$ is hydrogen.

9. A compound according to claim 1, having the formula

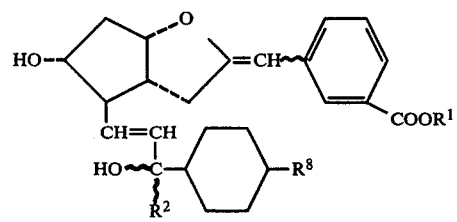

wherein $R^1$ and $R^2$ have the same meaning as in claim 1 and wherein $R^8$ represents hydrogen, methyl or ethyl.

10. A compound according to claim 1, having the formula

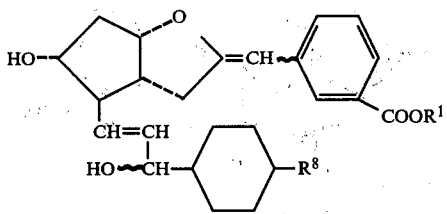

wherein $R^1$ has the same meaning as in claim 1 and wherein $R^8$ represents hydrogen, methyl or ethyl.

11. A compound according to claim 1, wherein $R^1$ represents a methyl or an ethyl group.

12. A compound according to claim 1, wherein $R^1$ represents a sodium or a potassium ion.

13. A compound according to claim 1, wherein the compound is the 15S-isomer.

14. A compound according to claim 1, comprising [(5EZ, 13E, 9α, 11α, 15S)-2,3,4-trinor-1,5-inter-m-phenylene-6,9-epoxy-11,15-dihydroxy-15-methyl]-prosta-5,13-dienoic acid, its pharmaceutically acceptable salts, and its methyl ester.

15. A compound according to claim 14, comprising the sodium salt of said compound.

16. A compound according to claim 1, comprising [(5EZ, 13E, 9α, 11α, 15S)-2,3,4-trinor-1,5-inter-m-phenylene-6,9-epoxy-11,15-dihydroxy-15-cyclohexyl-16,17,18,19,20-pentanor]-prosta-5,13-dienoic acid, its pharmaceutically acceptable salts, and its methyl ester.

17. A compound according to claim 16, comprising the sodium salt of said compound.

18. A pharmaceutical composition, comprising a therapeutically effective amount of a heterocyclic compound as defined by claim 1 as active ingredient and at least one pharmaceutically acceptable inert carrier or diluent.

19. A pharmaceutical composition according to claim 18, wherein the therapeutically effective amount is from about 0.01 to 10.0 mg per individual dose.

20. A pharmaceutical composition according to claim 18 or 19, suitable for parenteral administration and containing per individual dose from about 0.01 to 1.0 mg of said heterocyclic compound dissolved or suspended in a pharmaceutically acceptable carrier comprising a sterile liquid.

21. A pharmaceutical composition according to claim 18, or 19, for oral administration and containing per individual dose from about 0.1 to 10.1 mg of said heterocyclic compound and at least one solid pharmaceutically acceptable adjuvant.

22. A process for the preparation of a heterocyclic compound as defined by claim 1, comprising the steps of:

reacting a compound of the formula

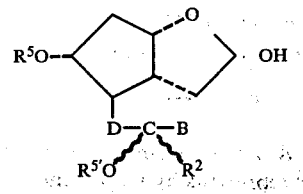

wherein B represents an alkyl group containing 5 to 9 carbon atoms and having the structure

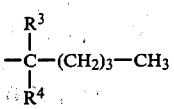

wherein $R^3$ and $R^4$ have the same or a different meaning and each represents hydrogen, methyl or ethyl, or B represents cyclohexyl or cyclohexyl substituted in position 4' by a methyl or an ethyl group, $R^2$ represents hydrogen or a methyl group, D represents —CH$_2$—CH$_2$—, (trans)—CH=CH— or CH=CHal—, in which Hal represents chlorine, bromine or iodine and wherein $R^5$ and $R^{5'}$ have the same or a different meaning and each represents hydrogen or a protecting group cleavable under mold conditions, in the absence of oxygen at about 10° to 30° C. in the presence of a solvent containing a strong base, with a compound of the formula

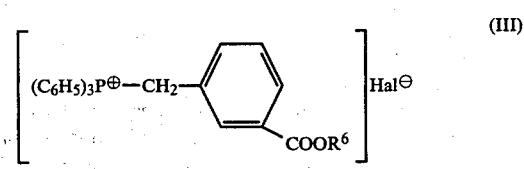

wherein $R^6$ is hydrogen or an alkyl group containing 1 to 6 carbon atoms, preferably methyl or ethyl, and wherein Hal represents chlorine, bromine or iodine; where $R^6$ is hydrogen, esterifying the group COOR$^6$ to the group COOR$^7$, wherein $R^7$ represents an alkyl group containing 1 to 6 carbon atoms; splitting off any protecting groups $R^5$ and $R^{5'}$ which are present under mild conditions to give a compound of the formula

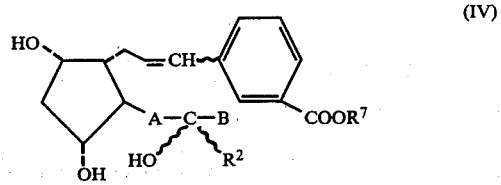

halogenating and cyclizing the compound of formula IV by treatment at about 0°-30° C. with an electrophilic brominating or iodinating agent in the presence of an inert solvent and in the presence of an agent capable of binding acids to give a compound of the formula

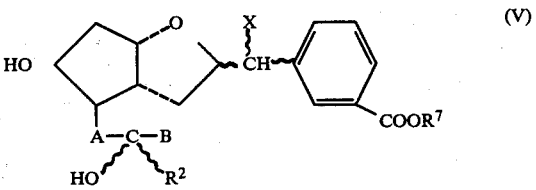

wherein A represents —CH$_2$CH$_2$—,(trans)—CH=CH— or —C≡C—, and X represents bromine or iodine; and dehydrohalogenating the compound of formula V to give a compound of the formula

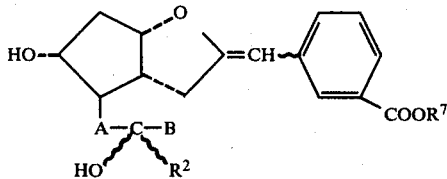 (Ia)

23. A process according to claim 22, further comprising the step of separating the product into its 5E- and 5Z isomers.

24. A process according to claim 22, wherein $R^5$ and $R^{5'}$ represent tetrahydropyranyl or a trimethylsilyl group.

25. A process according to claim 22, wherein said esterification step comprises reaction with diazomethane at a temperature between about 0° and 30° C.

26. A process according to claim 22, wherein is formula IV, $R^7$ represents methyl or ethyl.

27. A process according to claim 22, wherein said halogenation and cyclization is carried out additionally in the presence of water.

28. A process according to claim 22, wherein said dehydrohalogenation step comprises treating one mole of a compound of formula V with from about 1 to 5 moles of a base at a temperature between about 0° and 90° C.

29. A process according to claim 28, wherein said dehydrohalogenation step is carried out in the presence of a solvent.

30. A process according to claim 28, further comprising the step of saponifying the group $COOR^7$.

31. A process according to claim 30, wherein said saponification step comprises treating one mole of a compound of formula Ia in an aqueous alcoholic medium at a temperature of from about 10° to 50° C. with about 1 to 5 moles of an alkali hydroxide.

32. A process according to claim 22, wherein a compound of formula II is reacted with a compound of formula III in the presence of a catalytically effective amount of carboxylic acid.

33. A process according to claim 32, wherein said carboxylic acid comprises formic acid, acetic acid, propionic acid, bromoacetic acid, trichloroacetic acid, trifluoroacetic acid, phenylacetic acid, p-nitrobenzoic acid, p-chlorobenzoic acid, p-methoxybenzoic acid or benzoic acid.

34. A process according to claim 22, wherein in said halogenation and cyclization step a compound of formula IV is treated with iodine, iodine-potassium iodide or N-bromosuccinimide in presence of sodium hydrogen carbonate, sodium carbonate, magnesium oxide or calcium carbonate.

35. A process according to claim 30, wherein said dehydrohalogenation step of a compound of formula V is performed by means of treatment with a base comprising sodium hydroxide, potassium hydroxide sodium methoxide, sodium ethoxide, potassium tert.butoxide, triethylamine, dicyclohexylamine, 1,5-diazabicyclo-(4,3,0)-non-5-ene or 1,5-diazabicyclo-(5,4,0)-undec-5-ene.

36. A process according to claim 30 or 35, wherein the dehydrohalogenation of a compound of formula V and the saponification of the group $COOR^7$ are performed without intermediate isolation of a compound of formula Ia.

37. A process according to claim 22, further comprising separation of the RS-form of any of the compounds of formulae II, IV, V, Ia or I.

38. A process according to claim 37, wherein said isomer separation comprises a process using column chromatography.

39. A process according to claim 37, further comprising the step of separating a compound of formula IV into its 15S- and 15R-isomers by means of column chromatography, and then using only the 15S-isomer in the consecutive steps of the process.

40. A process according to claim 30, further comprising the step of subjecting the saponified product to ion exchange against an pharmaceutically acceptable cation by means of ion exchange chromatography.

41. A method for inhibiting blood platelet aggregation, comprising the step of administering to a human patient a blood platelet aggregation inhibiting amount of a compound as defined by claim 1.

42. A method for simultaneously inhibiting blood platelet aggregation and lowering blood pressure, comprising the step of administering to a human patient an amount of a compound as defined by claim 1, which is sufficient to simultaneously inhibit blood platelet aggregation and lower the blood pressure.

* * * * *

UNITED STATES PATENT AND TRADEMARK OFFICE
CERTIFICATE OF CORRECTION

PATENT NO. : 4,372,971
DATED : February 8, 1983
INVENTOR(S) : Ulrich Seipp et al.

It is certified that error appears in the above-identified patent and that said Letters Patent is hereby corrected as shown below:

IN THE SPECIFICATION

Column 6, line 4, after "considered" insert -- as --.

Column 7, line 31, after "diseases" insert -- in --.

IN THE SPECIFICATION AND ABSTRACT

In formulae I, II, V and Ia close the right hand ring to connect the bond and the oxygen atom.

IN THE CLAIMS

Column 19, claim 21, line 50, delete "10.1" and insert --10.0--.

Column 19, claim 22, formula II, insert a bond between carbon atom 6 and the hydroxy group.

Column 20, claim 22, line 17, delete "mold" and insert -- mild --.

Signed and Sealed this

Twenty-sixth Day of July 1983.

[SEAL]

Attest:

GERALD J. MOSSINGHOFF

Attesting Officer   Commissioner of Patents and Trademarks